United States Patent [19]

Mohan et al.

[11] Patent Number: 5,610,301

[45] Date of Patent: Mar. 11, 1997

[54] PROCESS FOR THE REGIOSELECTIVE N-ALKYLATION OF QUINAZOLINONES

[75] Inventors: Arthur G. Mohan, Somerville; Joseph D'Antuono, III, Three Bridges, both of N.J.

[73] Assignee: American Cyanamid Company, Madison, N.J.

[21] Appl. No.: 87,625

[22] Filed: Jul. 1, 1993

[51] Int. Cl.$^6$ ...................... C07D 239/88; C07D 239/92
[52] U.S. Cl. ............................. 544/284; 544/287
[58] Field of Search ...................... 544/284, 287

[56] References Cited

FOREIGN PATENT DOCUMENTS

| 253310 | 1/1988 | European Pat. Off. . |
| 443568 | 8/1991 | European Pat. Off. . |
| 497150 | 8/1992 | European Pat. Off. . |

*Primary Examiner*—Matthew V. Grumbling
*Attorney, Agent, or Firm*—T. S. Szatkowski

[57] ABSTRACT

A process for the regioselective N-alkylation of 2-alkyl-5, 6,7 or 8-substituted-4(3H)-quinazolinones in the presence of lithium salts.

5 Claims, No Drawings

PROCESS FOR THE REGIOSELECTIVE N-ALKYLATION OF QUINAZOLINONES

BACKGROUND OF THE INVENTION

1. Field of the Invention

The invention relates to a process for the regioselective N-alkylation of 2-alkyl-5,6,7 or 8-substituted-4(3H)-quinazolinones in the presence of lithium salts to give 2-alkyl-3-substituted-5,6,7 or 8-substituted-4(3H)-quinazolinones. This process has the advantages of providing a high yield of purer product in a more efficient and less costly way.

2. Description of the Prior Art

The compounds prepared by the process of the present invention namely the 2-alkyl-3-substituted-5,6,7 or 8-substituted-4(3H)-quinazolinones compounds of the following Formula I:

Formula I where $R^1$, $R^2$ and X are defined hereinafter, are important intermediates useful in the preparation of therapeutic 2,3,6-substituted quinazolinones which are useful as angiotensin II receptor blocking agents. The 2,3,6-substituted quinazolinone compounds and uses for such compounds are described in European Patent Application No. EP-497150-A.

As described in this application, the usual method used to prepare these 3-substituted quinazolinones involves reacting compounds of the formula:

where $R^1$, and X are defined hereinafter, with an alkylating agent of the formula: $R^2Br$, where $R^2$ is as defined hereinafter, in the presence of bases such as potassium or sodium carbonate or potassium t-butoxide. However, a significant amount of the isomeric O-alkylated compound of the formula:

where $R^1$, $R^2$ and X are defined hereinafter, is formed and is in many cases difficult to remove from the desired product.

Accordingly, this prior art process for the preparation of 2-alkyl-3-substituted-6-substituted-4(3H)-quinazolinones generally give rise to appreciable quantities of undesired by-products.

It has now been found that 2-alkyl-3-substituted-5,6,7 or 8-substituted-4(3H)-quinazolinone compounds may be advantageously synthesized via reaction of the appropriate alkylating reagent in the presence of lithium salts to produce the desired N-alkylated product without the presence of O-alkylated contaminates.

SUMMARY OF THE INVENTION

It is therefore an object of the present invention to provide an improved process for the manufacture of 2-alkyl-3-substituted-5,6,7 or 8-substituted-4(3H)-quinazolinones.

Upon further study of the specification and appended claims, further objects and advantages of this invention will become apparent to those skilled in the art.

It has now been discovered that the use of lithium methoxide, lithium hydroxide or lithium diisopropylamide in the alkylation of 2-alkyl-5,6,7 or 8-substituted-4(3H)-quinazolinones unexpectedly yields only 3-substituted product and none or minor amounts of the O-alkylated impurities.

The 2-alkyl-3-substituted-5,6,7 or 8-substituted-4(3H)-quinazolinones which may be prepared by this method may be represented by the following structural Formula I:

Formula I wherein;

$R^1$ is a straight or branched alkyl of 1 to 9 carbon atoms, optionally substituted with one to three substituents selected from H, straight chain alkyl of 1 to 4 carbon atoms, pyridine, thiophene, furan, O-straight chain alkyl of 1 to 4 carbon atoms, OH, O-acyl with a straight chain alkyl of 1 to 4 carbon atoms, halogen, phenyl, substituted phenyl (substitution selected from mono lower alkyl of 1 to 3 carbon atoms, —$CF_3$, nitro, O-alkyl of 1 to 3 carbon atoms, and $NH_2$);

$R^2$ is selected from a moiety of the formula:

C(Phenyl)$_3$, lower alkyl, benzyl optionally substituted with halogen (bromo, chloro or iodo) or cyanophenyl; and X is a straight chain alkyl of 1 to 6 carbon atoms. Relative to the above generic description, compounds of Formula I which are preferred are those in which:

$R^1$ is selected from moieties of the formulae:

$$-(CH_2)_n-\underset{R^6}{\underset{|}{\overset{R^4}{\overset{|}{C}}}}-OR^5, \quad -\underset{R^6}{\underset{|}{\overset{R^4}{\overset{|}{C}}}}-OR^5$$

$$-(CH_2)_n-\underset{R^6}{\underset{|}{\overset{OR^5}{\overset{|}{C}}}}-R^6, \quad -(CH_2)_n-\underset{R^6}{\underset{|}{\overset{OR^5}{\overset{|}{C}}}}-CH_2R^7,$$

$$-\underset{R^6}{\underset{|}{\overset{OR^5}{\overset{|}{C}}}}-R^6, \quad -\underset{R^6}{\underset{|}{\overset{OR^5}{\overset{|}{C}}}}-CH_2R^7,$$

-continued

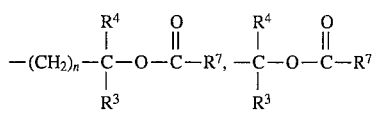

where $R^3$ is selected from H, straight chain lower alkyl of 1 to 4 carbon atoms, pyridine, thiophene, furan, halogen, phenyl and substituted phenyl (substitution selected from mono-lower alkyl of 1 to 3 carbon atoms, —$CF_3$, nitro, O-alkyl of 1 to 3 carbon atoms, and $NH_2$)

$R^4$ is selected from H, straight chain lower alkyl of 1 to 4 carbon atoms, phenyl, substituted phenyl (substitution selected from mono-lower alkyl of 1 to 3 carbon atoms, —$CF_3$, nitro, O-alkyl of 1 to 3 carbon atoms, and —$NH_2$), pyridine, thiophene, or furan; provided, however, that $R^3$ and $R^4$ cannot be H;

$R^5$ is H, straight chain or branched lower alkyl of 1 to 4 carbon atoms;

$R^6$ is straight chain lower alkyl of 1 to 4 carbon atoms, phenyl, substituted phenyl (substitution selected from mono-lower alkyl of 1 to 3 carbon atoms, —$CF_3$, nitro, O-alkyl of 1 to 3 carbon atoms, or —$NH_2$), pyridine, thiophene, or furan;

$R^7$ is straight or branched lower alkyl of 1 to 4 carbon atoms;

$R^2$ is selected from moieties of the formulae:

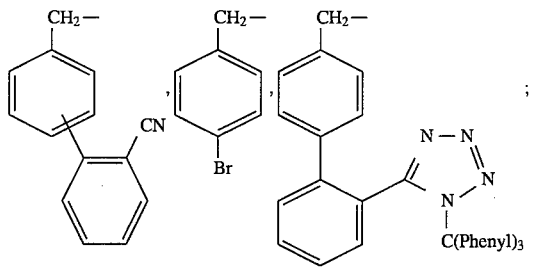

X is a straight chain alkyl of 1 to 6 carbon atoms; and n is an integer from 1 to 3.

Furthermore, the most preferred compounds of Formula I according to the present invention are those of Formula I in which:

$R^1$ is selected from moieties of the formulae:

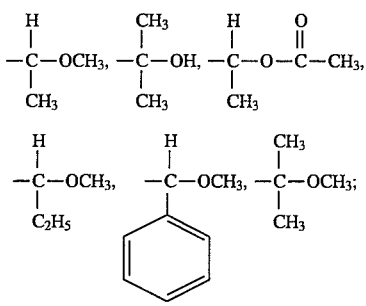

$R^2$ is selected from moieties of the formulae:

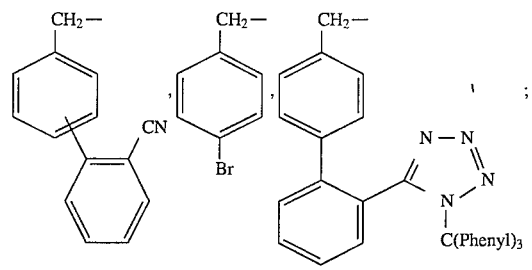

and X is a straight chain alkyl of 3 or 4 carbon atoms. Compounds of the Formula I which are most particularly preferred are those in which:

$R^1$ is selected from moieties of the formulae:

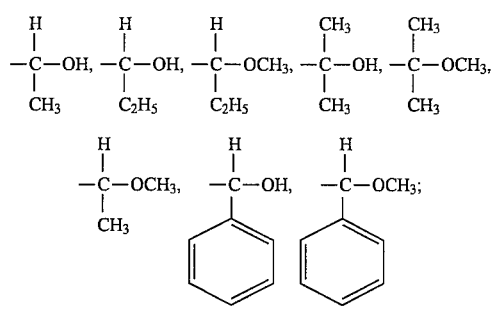

$R^2$ is selected from moieties of the formulae:

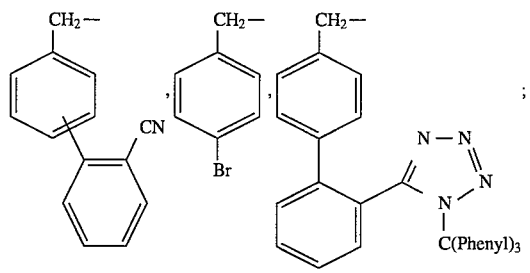

and X is a straight chain alkyl of 4 carbon atoms.

The improved process comprises reacting a 2-alkyl-5,6,7 or 8-substituted-4(3H)-quinazolinone having the formula:

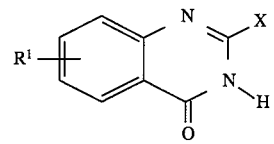

wherein $R^1$ and X are hereinbefore defined with an alkylating agent $R^2Z$ wherein $R^2$ is as hereinbefore described and Z is a leaving group such as Br, Cl, I, p-tolylsulfonyloxy-(tosyl), methylsulfonyloxy(mesyl) and the like;

in the presence of lithium methoxide, lithium hydroxide or lithium diisopropylamide and recovering the alkylated quinazolinone produced.

The reaction is preferably carried out in a suitable solvent such as tetrahydrofuran, N,N-dimethylformamide, N,N-dimethylacetamide, N-methylpyrrolidone, methanol, ethanol, t-butanol, dioxane or dimethylsulfoxide at a temperature of about 50° to 64° C. for about 1–49 hours.

DESCRIPTION OF THE PREFERRED EMBODIMENTS

The process and compounds of the present invention are described in the following reaction scheme I:

Scheme I

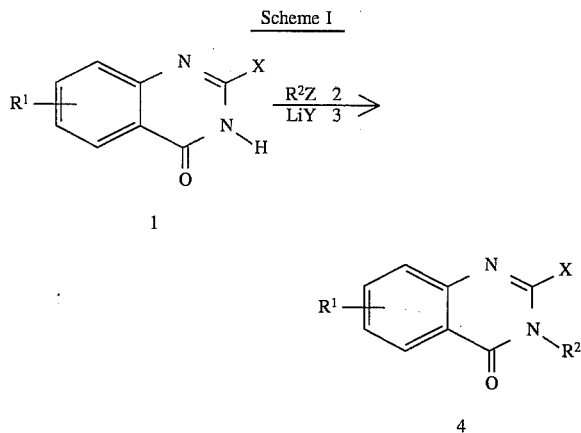

In accordance with the above reaction scheme I, 2-alkyl-5,6,7 or 8-substituted-4(3H)-quinazolinone 1, where $R^1$ and X is described above is preferably reacted with lithium salt 3 wherein Y is —OH, —OCH$_3$ or (iPr)$_2$N— in a suitable solvent such as tetrahydrofuran for about 1–2 hours at about 50° to 64° C. to give the lithium salt of 1 without isolation. The alkylating reagent 2 where $R^2$ and Z are described above is added and the reactants heated at a temperature from about 50° to about 64° C. The reaction solution is quenched with aqueous ammonium chloride and extracted with methylene chloride or partitioned between water and methylene chloride and the separated organic layer washed with aqueous sodium hydroxide. The organic layer is dried with magnesium sulfate to give a methylene chloride solution of the desired 2-alkyl-3-substituted-5,6,7 or 8-substituted-4(3H)-quinazolinone 4.

The above process is an improvement over the procedure described in the prior art. The distinct advantage being that none or minor amounts of the O-alkylated product is formed therefore giving product of higher purity, with easier and less labor and time intensive work-ups. Much time and labor is saved by not having to purify the products by chromatography.

The following specific examples are provided to further illustrate this invention and the manner in which it may be carried out. It will be understood, however, that the specific details given in the examples have been chosen for purposes of illustration and are not to be construed as a limitation on the invention.

EXAMPLE 1

4'-[[2'-Butyl-6-(1-hydroxy-1-methylethyl)-4-oxo-3(4H)-quinazolinyl]methyl]-[1,1'-biphenyl]-2-carbonitrile A mixture of 1900 g (7.30 mol) of 2-butyl-6-(1-hydroxy-1-methylethyl)-4(3H)-quinazolinone, and 277 g (6.96 mol) of lithium methoxide in 20 L of tetrahydrofuran is heated at reflux (63° C.) for one hour to give a clear amber solution. The reaction mixture is cooled to 50°–60° C. and 1894 g (6.960 mol) of 2-cyano-4'-bromomethylbiphenyl added, rinsing with 4 L of tetrahydrofuran. The reaction mixture is heated at reflux (64° C.) for 49 hours and cooled to ambient temperature. A solution of 1 Kg of ammonium chloride in 10 L of water is added and the mixture stirred for 15 minutes and the organic phase separated. The aqueous phase is extracted with two 10 L portions of dichloromethane and combined with the organic phase. The combined organic phases are extracted with 10 L of 0.5M sodium hydroxide followed by two 0.5 L washes with water. The organic phase is dried with 1 Kg of magnesium sulfate, the slurry filtered through 500 g of diatomaceous earth and the filter cake washed with two 2 L portions of dichloromethane. The solvent is partially evaporated to a volume of approximately 4 L and analyzed by HPLC to contain 88.2% (relative area %) of the desired product, 1.3% of 2-butyl-6-(1-hydroxy-1-methylethyl)-4(3H)-quinazolinone and 0.9% of 2-cyano-4'-bromo-methylbiphenyl. None of the O-alkylated product is detected by HPLC analysis.

EXAMPLE 2

3-[(Bromophenyl)methyl]-2-butyl-6-(1-methoxy-1-methylethyl)-4(3H)-quinazolinone

A slurry of 2.0 g (0.0077 mol) of 2-butyl-6-(1-hydroxy-1-methylethyl)-4-oxo-3(4H)-quinazolinone in 20 ml of tetrahydrofuran is treated with 0.320 g (0.0076 mol) of lithium hydroxide monohydrate and heated at reflux for 1.5 hours and 1.75 g (0.007 mol) of p-bromobenzyl bromide added and the mixture refluxed for 4 hours. The reaction mixture is cooled to ambient temperature and 10 ml of water added followed by 30 ml of dichloromethane. The mixture is extracted with two portions of 10% sodium hydroxide, the organic phase separated and the solvents evaporated in vacuo to an oily residue. The residue is dissolved in 20 ml of dichloromethane and washed two times with 25 ml portions of 1% sodium hydroxide. The organic layer is dried with magnesium sulfate and evaporated in vacuo to a residue. The residue is treated with a mixture of 5 ml of hexanes and 5 ml of ethyl acetate. The resulting solid is filtered to give 1.42 g (44.5%) of the desired product as a white crystalline solid. m.p. 121°–122° C.

EXAMPLE 3

2'-[2-Butyl-6-iodo-4-oxo-3(4H)quinazolinyl]-methylphenyl]benzonitrile

A mixture of 3.13 g (9.55 mmol) of 2-butyl-6-iodo-4-oxo-3(4H)quinazolinone and 0.401 g (9.55 mmol) of lithium hydroxide monohydrate in 100 ml of tetrahydrofuran is heated at reflux until all dissolves. To this complete solution is added 4.96 g (9.55 mmol) of 2-(4'-bromomethylphenyl)benzonitrile and the mixture heated at reflux for 25 hours. The reaction mixture is cooled to ambient temperature and 25 ml of 10% HCl added and the phases separated. The organic phase is diluted with 50 ml of dichloromethane, the solution dried over magnesium sulfate, filtered and concentrated in vacuo to a residue. The residue is diluted with dichloromethane and filtered. The filtrate is evaporated to give 4.37 g (88.2%) of the desired product as a white solid, softens at 95° C., melts 105°–113° C.

EXAMPLE 4

4'-[[2'-Butyl-6-(1-hydroxy-1-methylethyl)-4-oxo-3(4H)-quinazolinyl]methyl]-[1,1-biphenyl]-2-carbonitrile A mixture of 0.106 g (0.4 mmol) of 2-butyl-6-(1-hydroxy-1-methylethyl)-4(3H)-quinazolinone in 8 ml of dry tetrahydrofuran is stirred under inert gas while 0.20 ml of a 2M solution of lithium diisopropylamide (0.4 mmol) is added. To the clear colorless solution is added 0.109 g of 2-cyano-4'-bromomethylbiphenyl followed by heating the reaction mixture at reflux for 8 h. An additional 0.100 ml (0.2 mmol)

of 2M lithium diisopropylamide solution is added and the mixture heated at reflux for 3.5 h. The reaction mixture is neutralized with a few drops of 3M HCl and evaporated in vacuo to a residue. The residue is partitioned between 10 ml of water and 20 ml of methylene chloride. The organic layer is washed with 8 ml of 3M HCl followed by 20 ml of water. The volatiles are removed in vacuo to give 0.34 g of the desired product. HPLC analysis reveals 81.4% of the desired product and none of the isomeric O-alkylated material.

EXAMPLE 5

7-Chloro-2,3-dimethyl-4(3H)-quinazolinone

A mixture of 0.96 g (5.0 mmol) of 7-chloro-2-methyl-4(3H)-quinazolinone and 0.20 g (4.8 mmol) of lithium hydroxide monohydrate in 25 ml of tetrahydrofuran is heated at reflux with stirring for 0.5 h. After cooling to room temperature, 0.89 g (4.8 mmol) of methyl p-toluene sulfonate is added and the reaction mixture heated at reflux for 4 hours. The reaction mixture is neutralized with con. HCl and the solvent removed in vacuo to give a residue. The residue is slurried with 50 ml of water, filtered, washed with 50 ml of 0.5M sodium hydroxide, followed by (3×50 ml) of water. The solid is dried to give 0.73 g (73%) of the desired product, m.p. 162°–165° C. None of the isomeric O-alkylated product is detected by HPLC.

We claim:

1. A process for producing compounds of the formula:

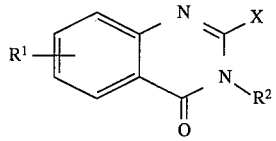

wherein $R^1$ is selected from moieties of the formula:

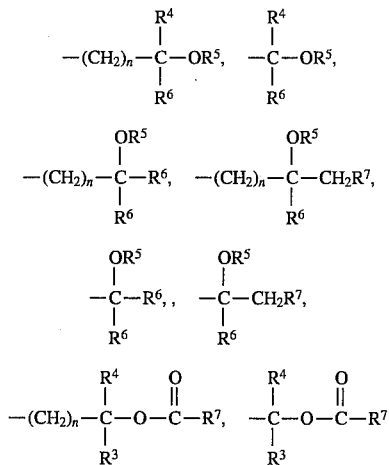

where $R^3$ is selected from H, straight chain lower alkyl of 1 to 4 carbon atoms, pyridine, thiophene, furan, halogen, phenyl and substituted phenyl (substitution selected from mono-lower alkyl of 1 to 3 carbon atoms, —$CF_3$, nitro, O-alkyl of 1 to 3 carbon atoms and $NH_2$); $R^4$ is selected from H, straight chain lower alkyl of 1 to 4 carbon atoms, pyridine, thiophene, furan, phenyl and substituted phenyl (substitution selected from mono-lower alkyl of 1 to 3 carbon atoms, —$CF_3$, nitro, O-alkyl of 1 to 3 carbon atoms, and —$NH_2$); provided, however, that $R^3$ and $R^4$ cannot both be H;

$R^5$ is selected from H, and straight chain or branched lower alkyl of 1 to 4 carbon atoms;

$R^6$ is selected from straight chain lower alkyl of 1 to 4 carbon atoms, pyridine, thiophene, furan, phenyl and substituted phenyl (substitution selected from mono-lower alkyl of 1 to 3 carbon atoms, —$CF_3$, nitro, O-alkyl of 1 to 3 carbon atoms, and —$NH_2$);

$R^7$ is straight or branched lower alkyl of 1 to 4 carbon atoms;

n is an integer from 1 to 3;

$R^2$ is selected from a moiety of the formula:

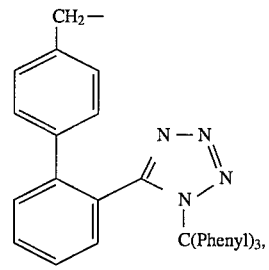

benzyl optionally substituted with halogen and cyanophenyl; and X is a straight chain alkyl of 1 to 6 carbon atoms which comprises:

a. reacting a 2-alkyl-5,6,7 or 8-substituted-4(3H)-quinazolinone having the formula:

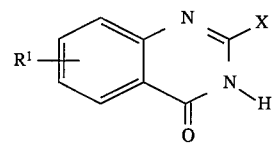

where $R^1$ is as defined above with an alkylating agent having the formula: $R^2Z$ where Z is a leaving group and $R^2$ is as defined above, in the presence of a lithium salt LiY where Y is —OH, —$OCH_3$ or $(iPr)_2N$—; and b. recovering the 2-alkyl-3-substituted-5,6,7 or 8-substituted-4 (3H)-quinazolinone.

2. The process according to claim 1 wherein X is a straight chain alkyl of 3 or 4 carbon atoms; $R^1$ is selected from moieties of the formulae:

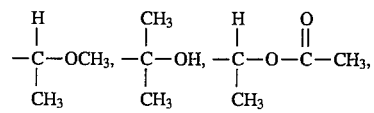

-continued

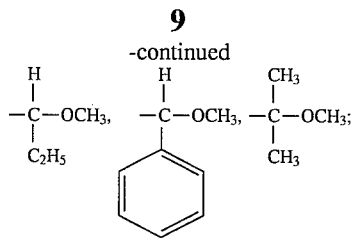

and R² is selected from moieties of the formulae:

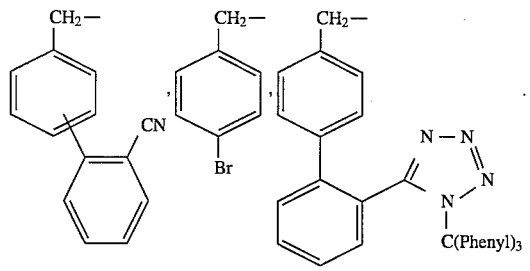

3. The process according to claim 1 wherein X is a straight chain alkyl of 4 carbon atoms; R¹ is selected from moieties of the formulae:

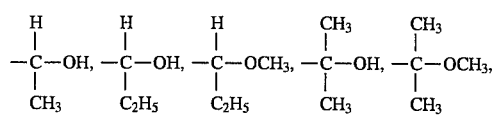

-continued

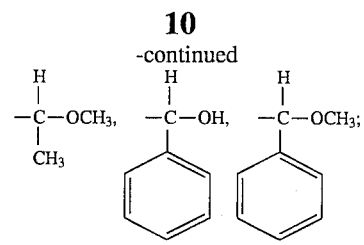

and R² is selected from moieties of the formulae:

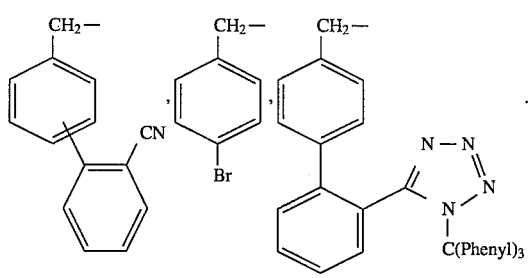

4. The process of claim 1 where the process is carried out at a temperature from about 50° to about 64° C.

5. The process of claim 1 wherein the reaction is carried out in tetrahydrofuran as a solvent.

\* \* \* \* \*